(12) United States Patent
Beebe et al.

(10) Patent No.: US 8,795,259 B2
(45) Date of Patent: Aug. 5, 2014

(54) DRUG DELIVERY PLATFORM INCORPORATING HYDROGEL PUMPING MECHANISM WITH GUIDED FLUID FLOW

(75) Inventors: David J. Beebe, Monona, WI (US);
Benjamin J. Moga, Madison, WI (US);
Tony Escarcega, Madison, WI (US);
Kent Chase, Sun Prairie, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 505 days.

(21) Appl. No.: 12/184,632

(22) Filed: Aug. 1, 2008

(65) Prior Publication Data

US 2010/0030156 A1    Feb. 4, 2010

(51) Int. Cl.
    A61K 9/22    (2006.01)
(52) U.S. Cl.
    USPC ...................................................... 604/890.1
(58) Field of Classification Search
    USPC ............... 604/890.1–892.1, 65–67, 131–133, 604/151, 153
    See application file for complete search history.

(56) References Cited

U.S. PATENT DOCUMENTS

| | | | |
|---|---|---|---|
| 4,552,561 A | | 11/1985 | Eckenhoff et al. |
| 4,556,086 A | | 12/1985 | Raines |
| 4,886,499 A | * | 12/1989 | Cirelli et al. ................ 604/131 |
| 5,109,850 A | | 5/1992 | Blanco et al. |
| 5,224,843 A | | 7/1993 | Van Lintel |
| 5,693,018 A | | 12/1997 | Kriesel et al. |
| 5,716,343 A | | 2/1998 | Kriesel et al. |
| 5,814,020 A | * | 9/1998 | Gross ........................ 604/141 |
| 5,928,194 A | * | 7/1999 | Maget ........................ 604/141 |
| 5,935,593 A | | 8/1999 | Ron et al. |
| 6,268,161 B1 | | 7/2001 | Han et al. |
| 6,416,495 B1 | | 7/2002 | Kriesel et al. |
| 6,475,750 B1 | | 11/2002 | Han et al. |
| 6,485,461 B1 | | 11/2002 | Mason et al. |
| 6,514,689 B2 | | 2/2003 | Han et al. |
| 6,523,559 B2 | | 2/2003 | Beebe et al. |
| 6,689,100 B2 | | 2/2004 | Connelly et al. |
| 7,074,915 B2 | | 7/2006 | Soreq et al. |
| 2002/0063060 A1 | | 5/2002 | Gascoyne et al. |
| 2002/0117517 A1 | | 8/2002 | Unger et al. |
| 2002/0193729 A1 | | 12/2002 | Cormier et al. |
| 2003/0187395 A1 | | 10/2003 | Gabel et al. |
| 2003/0187423 A1 | | 10/2003 | Wilkinson et al. |
| 2003/0196900 A1 | | 10/2003 | Chuang et al. |
| 2004/0068224 A1 | | 4/2004 | Couvillon et al. |
| 2004/0248326 A1 | | 12/2004 | Ziaie et al. |
| 2005/0038379 A1 | | 2/2005 | Beebe et al. |
| 2006/0002804 A1 | | 1/2006 | Jiang et al. |

FOREIGN PATENT DOCUMENTS

| | | |
|---|---|---|
| EP | 1086718 | 3/2001 |
| WO | 2008012788 | 1/2008 |
| WO | 2008083209 | 7/2008 |

\* cited by examiner

Primary Examiner — Kami A Bosworth
Assistant Examiner — Imani Hayman
(74) Attorney, Agent, or Firm — Boyle Fredrickson, S.C.

(57) ABSTRACT

A drug delivery platform is provided for delivering a controlled infusion of a drug to an individual. The drug delivery platform includes a reservoir for receiving the drug therein and a hydrogel engageable with the reservoir. The hydrogel is movable between a first configuration and a second configuration wherein the hydrogel exerts a pressure on the reservoir to urge the drug therefrom in response to a predetermined stimulus. A flow guide distributes the predetermined stimulus over the hydrogel in response to activation by an individual.

15 Claims, 6 Drawing Sheets

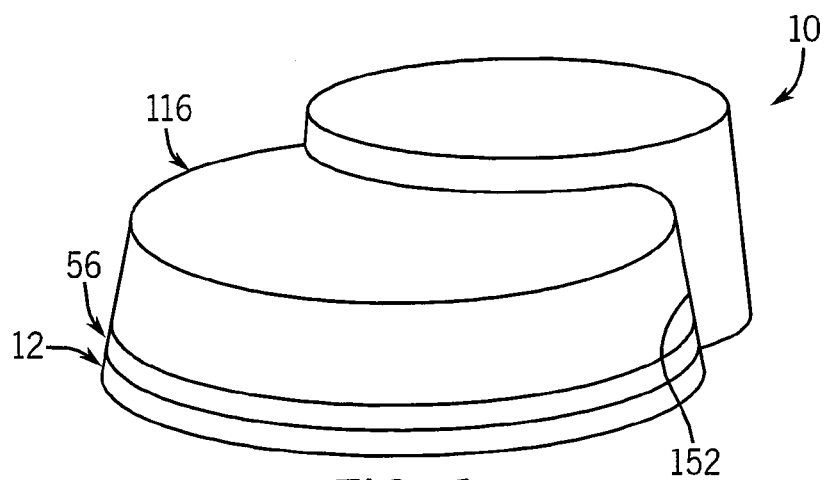
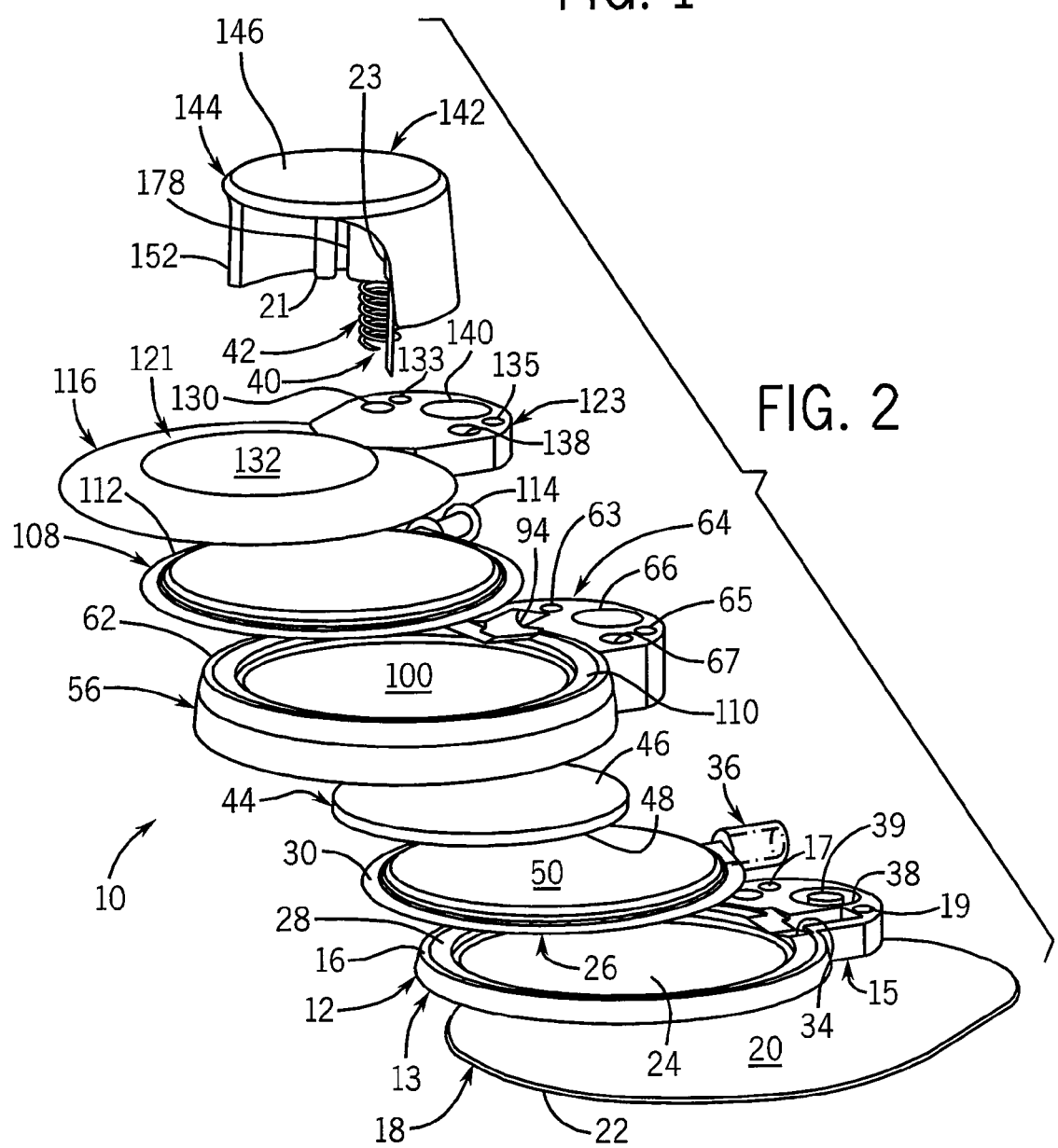

# DRUG DELIVERY PLATFORM INCORPORATING HYDROGEL PUMPING MECHANISM WITH GUIDED FLUID FLOW

FIELD OF THE INVENTION

This invention relates generally to microfluidic devices, and in particular, to a drug delivery platform utilizing a hydrogel pumping mechanism to provide controlled infusion of a drug to an individual.

BACKGROUND AND SUMMARY OF THE INVENTION

As is known, the pharmaceutical industry has had limited success overcoming the challenges of delivering pharmaceuticals to patients. The oral ingestion of pharmaceuticals is considered the safest, most convenient and most economical method of drug administration. As compared to present alternatives, patient acceptance and adherence to a dosing regimen is typically higher among orally delivered pharmaceuticals. However, the oral delivery of many pharmaceuticals is not possible because the pharmaceuticals are either too large or too electrically charged to pass through the small intestine to reach the bloodstream. In addition, many pharmaceuticals which are unable to withstand the environment of the digestive tract or to penetrate the dermis need to be injected into the patient (e.g. insulin, proteins).

In order to overcome the problems associated with orally delivered pharmaceuticals, transdermal drug delivery patches have been developed. Transdermal drug delivery patches incorporate a medication and are intended to adhere to the skin of an individual. Molecules of the medication pass through the skin and into the bloodstream of the individual thereby delivering a specific dose of medication. While functional for their intended purposes, these patches have certain inherent limitations. By way of example, since the skin is a very effect barrier, existing transdermal drug delivery patches can only be used to deliver small molecule drugs such as nicotine and birth control. Alternatively, other transdermal technologies have been developed that utilize pressurized gas or voltage to move larger drug molecules across the skin barrier into the bloodstream. Again, while functional for their intended purposes, use of these technologies are limited to smaller volume injections and may have the undesired effect of altering the medications supplied to individuals. Therefore, a transdermal drug delivery device that provides controlled infusion of a drug to an individual without the use of pressurized gas or voltage would constitute a significant advancement in the art.

Therefore, it is a primary object and feature of the present invention to provide a drug delivery device that provides controlled infusion of a drug to an individual without the use of pressurized gas or voltage.

It is a further object and feature of the present invention to provide a drug delivery device that provides controlled infusion of a drug to an individual while maximizing the volume of drug delivered.

It is a still further object and feature of the present invention to provide a drug delivery device that provides controlled infusion of a drug to an individual that is simple to utilize and inexpensive to manufacture.

In accordance with the present invention, a drug delivery platform is provided for delivering a controlled infusion of a drug to an individual. The drug delivery platform includes a reservoir for receiving the drug therein and a hydrogel engageable with the reservoir. The hydrogel is movable between a first configuration and a second configuration wherein the hydrogel exerts a pressure on the reservoir to urge the drug therefrom in response to a predetermined stimulus. A flow guide distributes the predetermined stimulus over the hydrogel in response to activation by an individual.

The predetermined stimulus is a fluid and the flow guide includes an input. The drug delivery platform includes an initiation fluid and an actuation mechanism movable between a non-actuated position and an actuated position wherein the initiation fluid is provided at the input of the flow guide. The activation mechanism includes an initiation conduit having an input and output. The input of the initiation conduit communicates with the initiation fluid and the output of the initiation conduit communicates with the input of the flow guide.

A barrier is provided between the initiation fluid and the pressure source. The barrier defines the flow guide. The flow guide includes a channel network formed in the barrier. The channel network includes a plurality of circular, concentric channels and a plurality of generally straight channels extending radially from a common point. The straight channels intersect at least one of the plurality of concentric, circular channels. The flow guide may also include a recessed surface formed in the barrier. The recessed surface extends about the plurality of circular, concentric channels. The flow guide may also include a fluid diverter. The fluid diverter directs fluid from the input of the flow guide to the channel network.

In accordance with a further aspect of the present invention, a drug delivery platform is provided for delivering a controlled infusion of a drug to an individual. The drug delivery platform includes an initiation fluid and a reservoir for receiving the drug therein. A hydrogel is engageable with the reservoir. The hydrogel is movable between a first configuration and a second configuration wherein the pressure source exerts a pressure on the reservoir to urge the drug therefrom in response to exposure to the initiation fluid. A barrier isolates the initiation fluid from the hydrogel. The barrier defines a channel network having an input and is in communication with the hydrogel. An actuation mechanism is movable between a non-actuated position and an actuated position wherein the initiation fluid is provided to the input of the channel network.

The actuation mechanism includes an initiation conduit having an input and output. The input of the initiation conduit communicates with the initiation fluid and the output of the initiation conduit communicates with the input of the channel network with activation mechanism in the actuated position. The channel network includes a plurality of circular, concentric channels and a plurality of generally straight channels extending radially from a common point. The straight channels intersect at least one of the plurality of concentric, circular channels. The barrier includes a recessed surface formed therein. The recessed surface extends about the plurality of circular, concentric channels. A fluid diverter projects from the recessed surface. The fluid diverter directs fluid to the input of the channel network.

In accordance with a still further aspect of the present invention, a drug delivery platform is provided for delivering a controlled infusion of a drug to an individual. The drug delivery platform includes a reservoir for receiving the drug therein and an expansion structure positioned adjacent the reservoir. The expansion structure is movable between a first configuration and an expanded second configuration wherein the expansion structure exerts a pressure on the reservoir to urge the drug therefrom in response to a predetermined stimulus. An actuation mechanism is movable between a non-actuated position and an actuated position. A barrier isolates the predetermined stimulus from the expansion structure. The barrier includes a flow guide for guiding the predetermined stimulus to the expansion structure in response to the actuation mechanism moving to the actuated position.

The expansion structure includes a hydrogel that expands in response to the predetermined stimulus, such as a fluid. The drug delivery platform may include an initiation fluid wherein the actuation mechanism includes an initiation conduit having an input and output. The input of the initiation conduit communicates with the initiation fluid and the output of the initiation conduit communicates with an input of the flow guide in response to the actuation mechanism moving to the actuated position.

The flow guide includes a channel network formed in the barrier. The channel network includes a plurality of circular, concentric channels and a plurality of generally straight channels extending radially from a common point. The straight channels intersecting at least one of the plurality of concentric, circular channels. The flow guide may also include a recessed surface formed in the barrier. The recessed surface extends about the plurality of circular, concentric channels. In addition, the flow guide may include a fluid diverter, the fluid diverter directing fluid from the input of the flow guide to the channel network.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiments.

In the drawings:

FIG. 1 is an isometric view of a drug delivery platform in accordance with the present invention;

FIG. 2 is an exploded view of the drug delivery platform of the present invention;

DETAILED DESCRIPTION OF THE DRAWINGS

Figure 3:
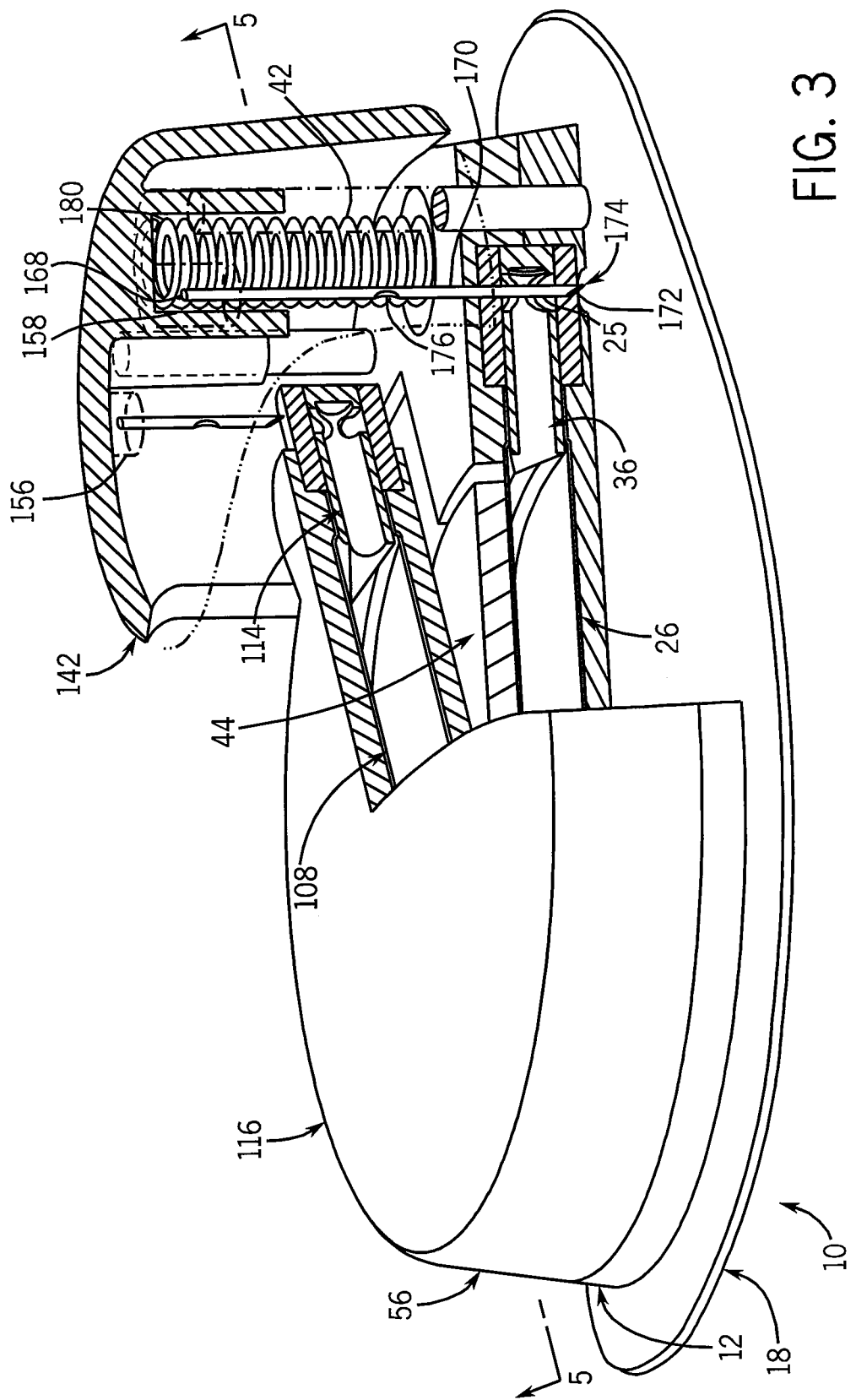
FIG. 3 is an isometric view, sectioned in two different planes, showing the drug delivery platform of the present invention in a non-actuated position.

Referring to FIG. 1, a drug delivery platform in accordance with the present invention is generally designated by the reference numeral 10. It is intended for drug delivery platform 10 to be affixed to an individual, as hereinafter described, to provide a controlled infusion of a drug to the individual. As best seen in FIGS. 2 and 5-7, drug delivery platform 10 includes base 12 having a generally circular body portion 13 and an ear portion 15 projecting radially from the outer periphery of body portion 13. Guide passageways 17 and 19 extend through ear portion 15 of base 12 to accommodate corresponding guide pins 21 and 23, respectively, for reasons hereinafter described. Base 12 further includes a generally flat lower surface 14 and an upper surface 16. Adhesive pad 18 includes an upper surface 20 affixed to lower surface 14 of base 12 in any conventional manner and a lower surface 22 having an adhesive thereon for interconnecting drug delivery platform 10 to an individual at a user desired location.

Upper surface 16 of body portion 13 of base 12 includes a generally circular recess 24 adapted for receiving bladder 26 therein. Generally circular groove 27 extends about the outer periphery of recess 24 and is adapted for receiving enlarged outer end 30a of lip 30 of bladder 26. Shoulder 28 extends radially inward from inner edge 27a of groove 27 for supporting lip 30 of bladder 26. Upper surface 16 of ear portion of base includes concave-shaped recess 34 adapted for receiving output end 36 of bladder 26. Needle passageway 25, FIGS. 3-4, interconnects concave-shaped recess 34 and lower surface 14 of base 12. In addition, circular recess 38 extends into upper surface 16 of ear portion 15 of base 12 and defines generally cylindrical support post 39. Support post 39 in recess 38 is adapted for receiving lower end 40 of spring 42 thereon, for reasons hereinafter described. Support post 39 may extend beyond upper 16 of ear portion 15 of base 12 to align the various components of drug delivery platform 10 of the present invention.

Drug delivery platform 10 further includes a pressure source such as hydrogel disc 44. Hydrogel disc 44 includes an upper surface 46 and a lower surface 48 interconnected by outer periphery 47. Hydrogel disc 44 is positionable on upper surface 50 of bladder 26 at a location adjacent end 52 opposite output end 36 of bladder 26, for reasons hereinafter described. It is contemplated for hydrogel disc 44 to expand in response to a predetermined stimulus such as exposure to a fluid or the like.

Drug delivery platform 10 further includes a barrier or middle insert 56 having a lower surface 60 receivable on upper surface 16 of base 12 so as to capture bladder 26 and hydrogel disc 44 therebetween and an upper surface 60. Middle insert 56 is further defined by a generally circular body portion 62 having an ear portion 64 projecting radially from the outer periphery thereof. Guide passageways 63 and 65 extend through ear portion 64 of middle insert 56 to accommodate corresponding guide pins 21 and 23, respectively, for reasons hereinafter described. Needle passageway 67 and spring passageway 66 also extend through ear portion 64 of middle insert 56 between upper and lower surfaces 58 and 60, respectively. Needle passageway 67 is axially aligned with concave-shaped recess 34 in upper surface 16 of base 12, while spring passageway 66 is axially aligned with circular recess 38 extending into upper surface 16 of ear portion 15 of base 12. Spring passageway 66 has a diameter sufficient to accommodate spring 42, for reasons hereinafter described.

As best seen in FIGS. 2 and 8-10, lower surface 60 of body portion 62 of middle insert 56 includes a generally circular recess 68 terminating at inner terminal surface 80. Generally circular groove 70 extends about the outer periphery of recess 68 and is adapted for receiving enlarged edge 30a of lip 30 of bladder 26, FIGS. 5-7. Shoulder 72 extends radially inward from inner edge 70a of groove 70. Lower surface 60 of ear portion 64 of middle insert 56 further includes concave-shaped recess 74 extending radially outwardly from inner edge 72a of shoulder 72. Concave-shaped recess 74 is adapted for receiving output end 36 of bladder 26. Needle passageway 76 extends between upper surface 58 of middle insert 56 and concave-shaped output recess 74, for reasons hereinafter described.

Terminal surface 80 of recess 68 in body portion 62 of middle insert 56 includes defined by concentric inner and outer, generally circular, flow channels 82a and 82b, respectively. Recessed portion 84 of terminal surface 80 extends about and is radially spaced from outer flow channel 82b. A plurality of spokes 86a-86e extend from a common point 88 located at the center of inner flow channel 82a so as to interconnect recessed portion 84 of terminal surface 80 with inner and outer flow channels 82a and 82b, respectively. Recessed portion 84 of terminal surface 80 communicates with a needle passageway 90 through input channel 92. Needle passageway 90, in turn, communicates with concave-shaped recess 94 in upper surface 58 of ear portion 64 of middle insert 56. Flow diverter 96 projects from recessed portion 84 of terminal surface 80 at a location between input 92 and outer flow channel 82b. In the depicted embodiment, flow diverter 96 is generally crescent-shaped. However, other shapes are possible without deviating from the scope of the present invention.

Figure 9:
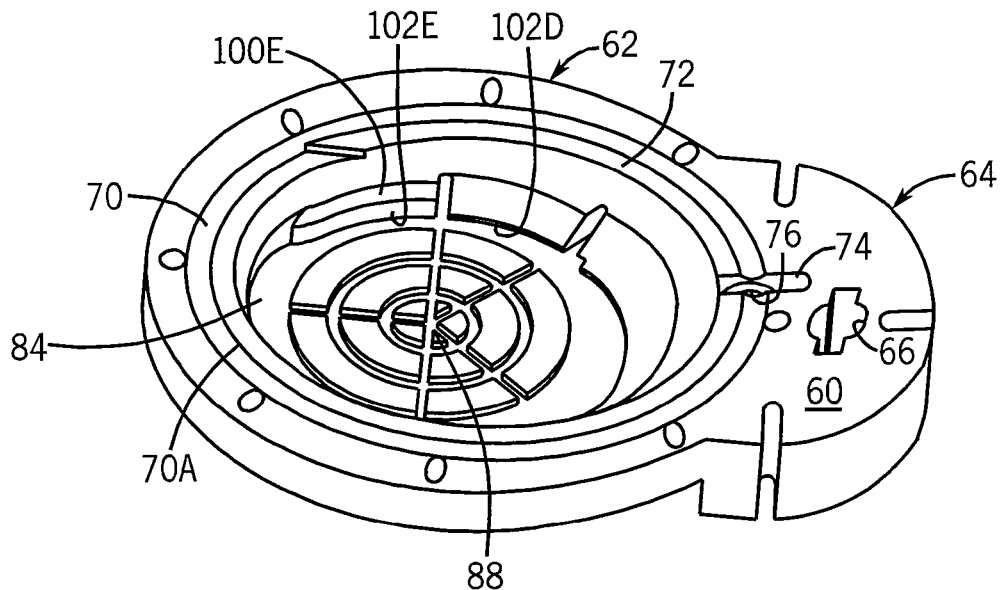
FIG. 9 is a bottom, isometric view of the middle insert of the drug delivery platform of the present invention taken from a first side of the middle insert.
Figure 10:
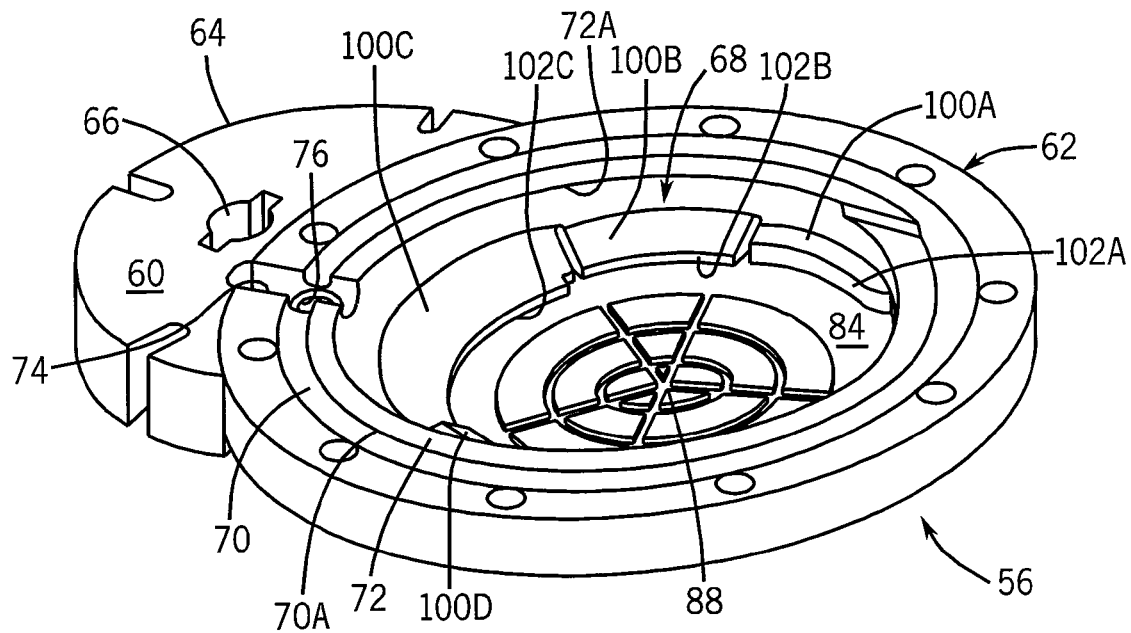
FIG. 10 is a bottom, isometric view of the middle insert of the drug delivery platform of the present invention taken from a second side of the middle insert.

Referring specifically to FIGS. 9-10, a plurality of circumferentially spaced ledges 100a-100e project from terminal surface 80 of middle insert 56. Inner edges 102a-102b of ledges 100a-100e, respectively, are intended to align hydrogel disc 44 captured between bladder 26 and middle insert 56 of drug delivery platform 10, as hereinafter described.

Referring back to FIGS. 2 and 5-7, upper surface 58 of body portion 62 of middle insert 56 includes a generally circular recess 106 adapted for receiving a storage structure or bladder 108 therein. Shoulder 110 extends about the outer periphery of recess 106 and is adapted for receiving peripheral edge 112 of bladder 108 thereon. Recess 106 communicates with concave-shaped recess 94, which in turn, is adapted for receiving output end 114 of bladder 108.

Cover 116 is receiveable on upper surface 58 of middle insert 56. Cover 116 includes an upper surface 132 and a lower surface 120. Cover 116 is further defined by a generally circular body portion 121 and an ear portion 123 projecting radially from the outer periphery of body portion 121. Lower surface 120 of body portion 121 has a recess 122 therein adapted for receiving bladder 108. Shoulder 124 extends about the outer periphery of recess 122 and is adapted for engaging peripheral edge 112 of bladder 108. In addition, lower surface 120 of ear portion 123 of cover 116 includes a concave-shaped recess 128 for accommodating output end 114 of bladder 108. Needle passageway 130 extends between concave-shaped recess 128 in lower surface 120 of cover 116 and upper surface 132 of cover 116, for reasons hereinafter described.

Ear portion 123 of cover 116 further includes guide passageways 133 and 135 extending therethrough for accommodating corresponding guide pins 21 and 23, respectively, for reasons hereinafter described. Needle passageway 138 and spring passageway 140 also extend through ear portion 123 of cover 116 between upper and lower surfaces 132 and 120, respectively. Needle passageway 138 is axially aligned with concave-shaped recess 94 in upper surface 58 of middle insert 56, while spring passageway 140 is axially aligned with spring passageway 66 through ear portion 64 of middle insert 56 and with circular recess 38 extending into upper surface 16 of ear portion 15 of base 12. Spring passageway 140 has a diameter sufficient to accommodate spring 42, for reasons hereinafter described.

Figure 4:
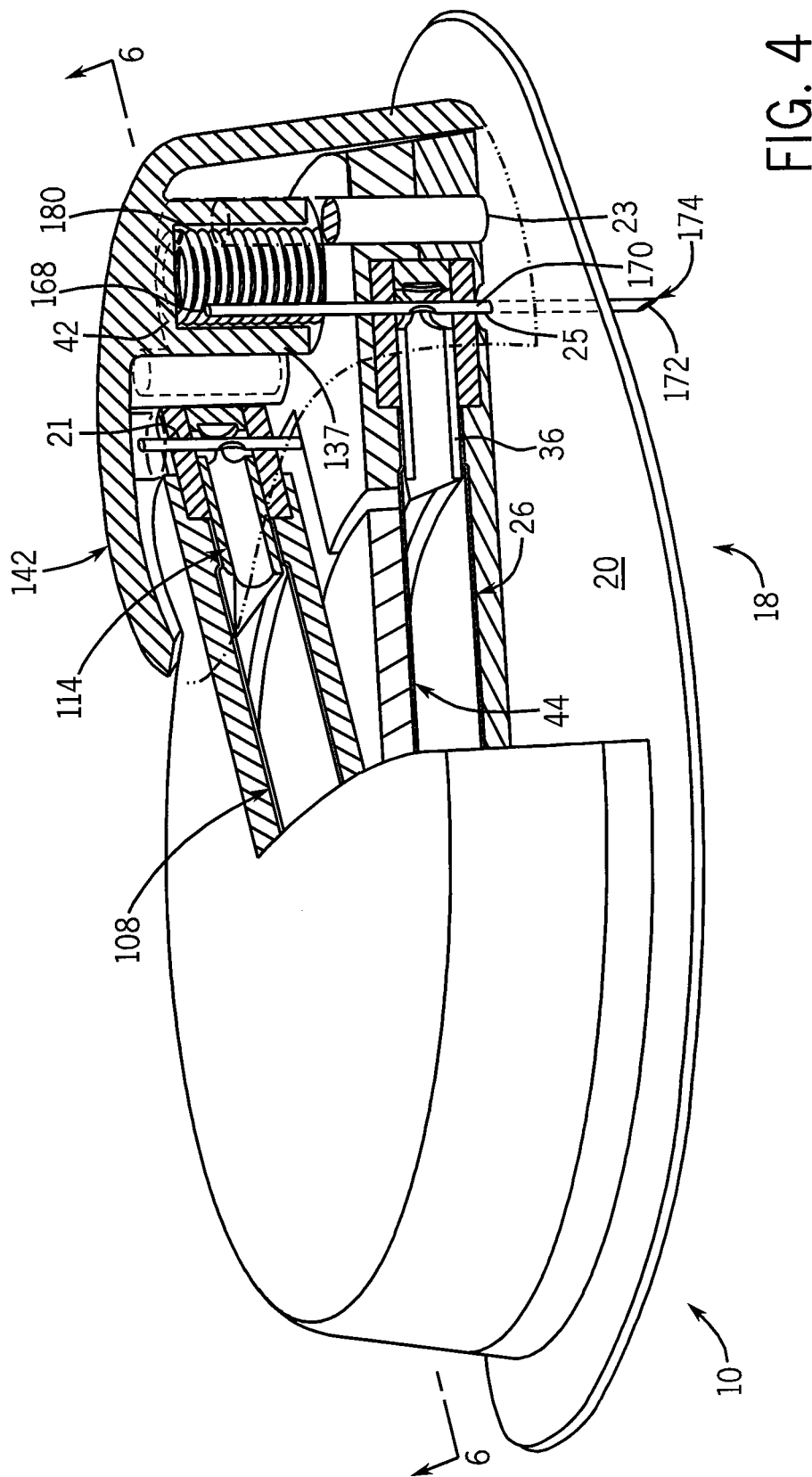
FIG. 4 is an isometric view, sectioned in two different planes, showing the drug delivery platform of the present invention in an actuated position.
Figure 5:
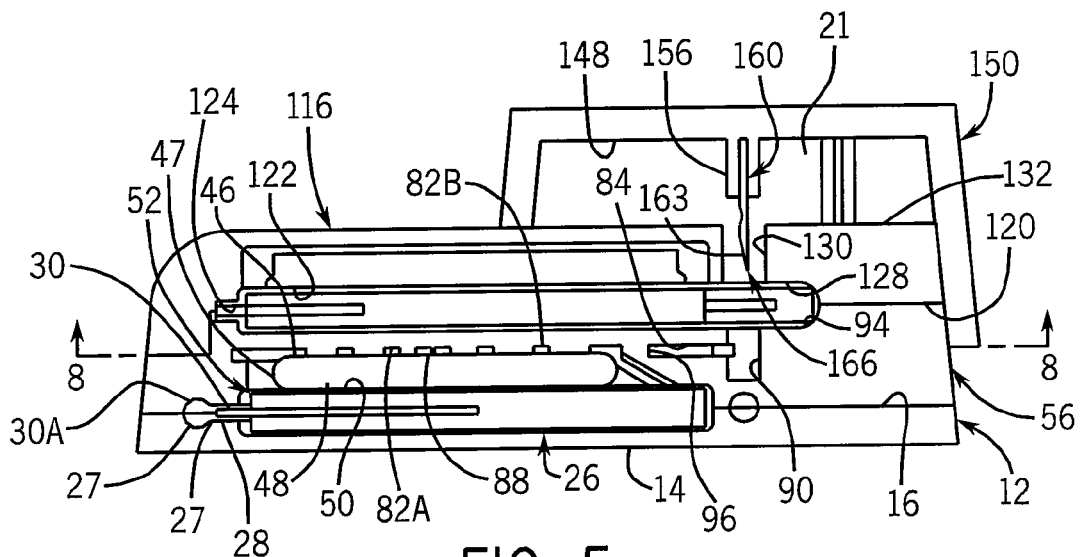
FIG. 5 is a cross sectional view of the drug delivery platform of the present invention taken along line 5-5 of FIG. 3.
Figure 6:
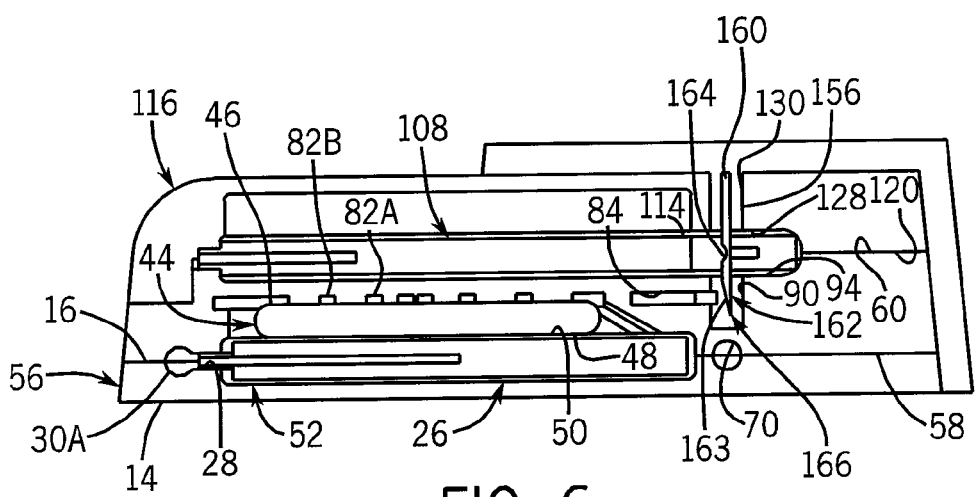
FIG. 6 is a cross sectional view of the drug delivery platform of the present invention taken along line 6-6 of FIG. 4.
Figure 7:
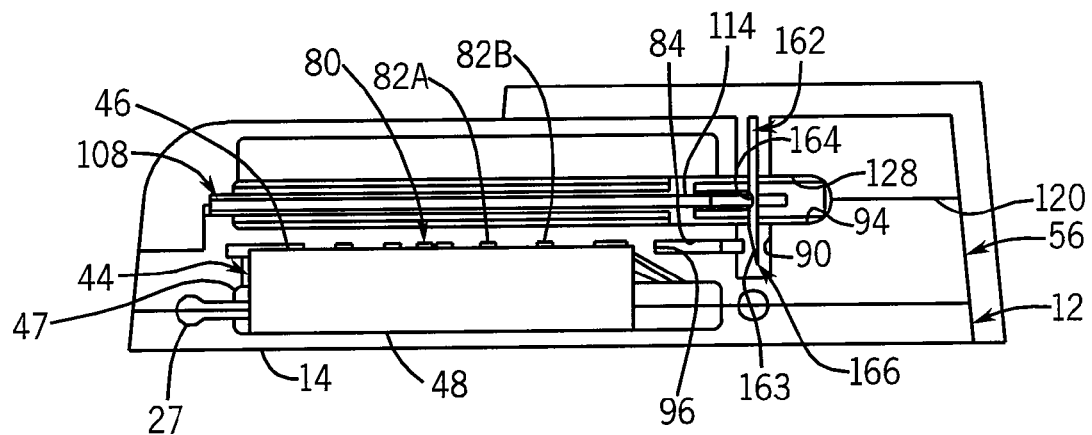
FIG. 7 is a cross sectional view of the drug delivery platform of the present invention, similar to FIG. 5, with the pressure source in an expanded configuration.
Figure 8:
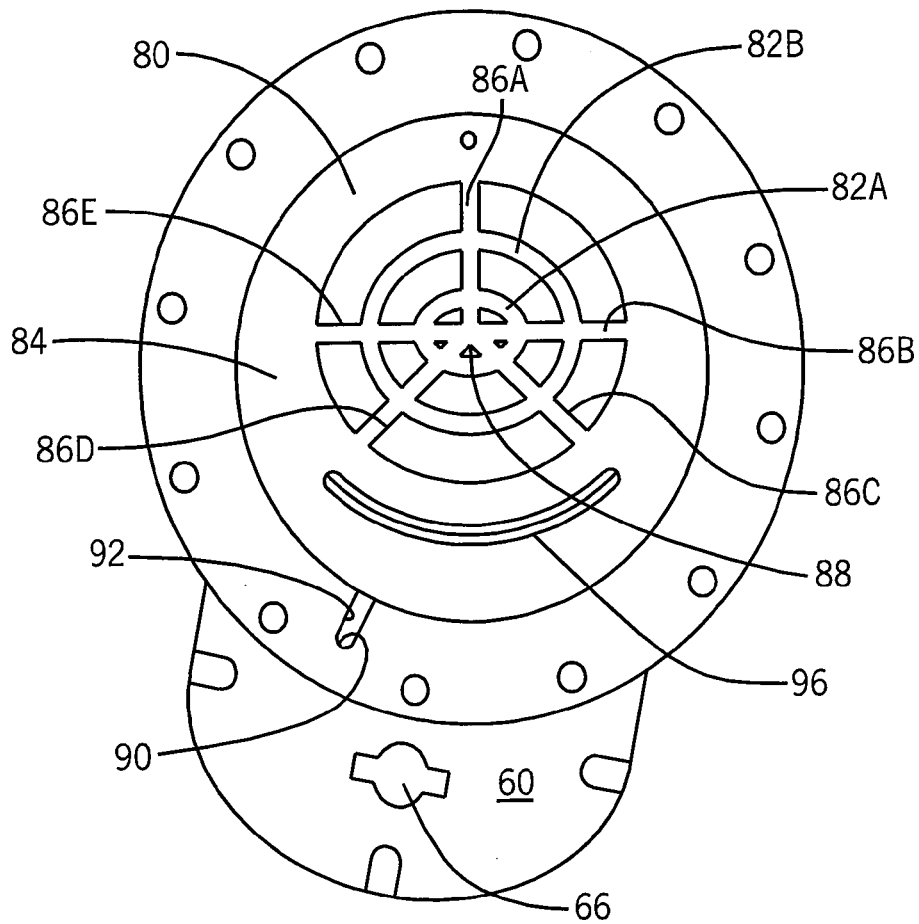
FIG. 8 is a cross sectional view of a middle insert for the drug delivery platform of the present invention taken along line 8-8 of FIG. 2.

In order to actuate drug delivery platform 10, initiation button 142 is provided. Initiation button 142 includes a generally flat base 144 having an upper surface 146 and a lower surface 148. Guide wall 150 depends from the outer periphery of base 142 and extends about the outer periphery of ear portion 123 of cover 116. Guide wall 150 includes recess 152 therein so as to allow base portion 144 of initiation button 142 to partially overlap upper surface 132 of cover 116. Guide pins 21 and 23 depend from lower surface 148 and are slidably received in corresponding guide passageways 133 and 135, respectively, to guide movement of initiation button 142 between a non-actuated position, FIGS. 3 and 5, and an actuated position, FIGS. 4 and 6-7. It is noted that initiation button 142 may include third guide pin 137, FIGS. 3-4, for further guiding movement of initiation button 142 between the non-actuated and actuated positions. Cover 116 further includes first and second, generally tubular, needle supports 156 and 158, respectively, depending from lower surface 148 of base 144. First needle support 156 is adapted for receiving upper end 160 of initiation needle 162. First needle support 156 is axially aligned with and has a diameter less than needle passageway 130 through cover 116. As best seen in FIGS. 5-7, initiation needle 162 includes an output 163 at lower end 166 thereof and an input 164 centrally located between upper end 160 and lower end 166 thereof.

Second needle support 158 is adapted for receiving upper end 168 of output needle 170. Referring to FIGS. 3-4, output needle 170 includes an output 172 at lower end 174 thereof and an input 176 at a location between upper end 168 and lower end 174 thereof. Output needle 170 extends through needle passageway 138 in cover 116; needle passageway 67 through middle insert 56; output end 36 of bladder 26; and needle passageway 25 through base 12. It can be appreciated that the outer surface of output needle 170 and output end 36 of bladder 26 form a fluid-tight relationship for maintaining a drug in bladder 26 when drug delivery device is not actuated, as hereinafter described.

Initiation button 142 further includes a generally tubular spring retainer 178 depending from lower surface 148 of base 144 and adapted for receiving upper end 180 of spring 42 therein. Spring 42 passes through spring passageway 140 in cover 116; spring passageway 66 in middle insert 56; and into recess 38 in base 12 about support post 39. As described, it can appreciated that initiation button 142 is movable between the first non-actuated position, FIGS. 3 and 5, and the second actuated position, FIGS. 4 and 6-7, against the bias of spring 42.

In operation, the drug delivery platform 10 is assembled as heretofore described wherein bladder 108 is filled with a fluid to which hydrogel disc 44 is responsive and bladder 26 is filled with a predetermined drug. Lower surface 22 of adhesive pad 18 is affixed to an individual at a desired location so as to interconnect drug delivery platform 10 to the individual. Referring to FIGS. 3 and 5, with initiation button 142 in its non-actuated state, input 164 of initiation needle 162 is isolated from output end 114 of bladder 108 and such that output 163 of initiation needle 162 is isolated from input 192 to recess surface 84 of terminal surface 80 of middle insert 56. In addition, with initiation button 142 in the non-actuated position, input 176 of output needle 170 is isolated from output end 36 of bladder 26 and output 172 of output needle 170 is isolated from the individual to which the drug in bladder 26 is to be administered.

Referring back to FIGS. 4 and 6, in order to actuate a drug delivery platform 10, initiation button 142 is pressed against the bias of spring 42 such that initiation needle 162 pierces output end 114 of bladder 108. As a result, input 164 of initiation needle 162 communicates with the interior of bladder 108 via output end 114 and output 163 of initiation needle 162 communicates with input channel 92 of recessed portion 84 of terminal surface 80 in middle insert 56. In addition, with initiation button 142 in the actuated position, input 176 of output needle 170 communicates with the interior of bladder 26 through output end 36 and output 172 of output needle 170 is received within the individual to which the drug is to be administered.

Referring to FIG. 7, with initiation button 142 in the actuated position, fluid flows from the interior of bladder 108 into initiation needle 162 through input 164 thereof. The fluid exits initiation needle 162 through output 163 and flows onto recessed portion 84 of terminal surface 80 through input channel 92. Flow diverter 96 causes the fluid to flow about the entirety of recessed portion 84 of terminal surface 80 into spokes 86a-86b, thereby directing the fluid into flow channels 82a and 82b. Thereafter, the fluid is distributed onto a substantial portion of upper surface 46 of hydrogel disc 44 and about the outer periphery thereof. It can be appreciated that recessed portion 84 of terminal surface 80, flow diverter 96, flow channels 82a and 82b, and spokes 86a-86e act as a flow guide to guide fluid from output 163 of initiation needle 162 to hydrogel disc 44. In response, hydrogel disc 44 expands thereby providing pressure onto bladder 26. Flow diverter 96 acts to prevent hydrogel disc 44 from expanding in such a manner as to block input channel 92 and prevent additional fluid from flowing onto recessed portion 84 of terminal surface 80 therethrough. As heretofore described, hydrogel disc 44 is positioned adjacent end 52 of bladder 26 such that expansion of hydrogel disc 44 urges the drug within bladder 56 toward output end 36 thereof. Under pressure, the drug flows from the output end 36 of bladder 26 into output needle 70 through input 176 thereof. Thereafter, the drug exits output needle 170 through output 172 and is dispensed into the individual.

It can be appreciated that since the rate of expansion of hydrogel disc 44 controls the flow rate of the drug from bladder 26 into the individual, the desired delivery profiles such as bolus injections, constant infusion, delayed onset or the like are possible simply by altering the chemistry of hydrogel disc 44. It can also be appreciated the output 172 of output needle 170 can be replaced with a microneedle array or like without deviating from the scope of the present invention.

Various modes of carrying out the invention are contemplated as being within the scope of the following claims particularly pointing and distinctly claiming the subject matter that is regarded as the invention.

We claim:

1. A drug delivery platform for delivering a controlled infusion of a drug to an individual, comprising:
    a reservoir for receiving the drug therein;
    a hydrogel engageable with the reservoir, the hydrogel movable between a first configuration and a second configuration wherein the hydrogel exerts a pressure on the reservoir to urge the drug therefrom in response to exposure of the hydrogel to an activation fluid ;
    a storage structure housing the activation fluid, the activation fluid in the storage structure being fluidicly isolated from the hydrogel;
    an activation mechanism movable between a first position wherein the activation fluid is fluidicly isolated from the hydrogel and second position wherein the activation fluid is in fluidic communication with the hydrogel; and
    a flow guide for guiding the activation fluid from the storage structure to the hydrogel with the activation mechanism in the second position, the flow guide having an input;
    wherein the actuation mechanism includes an initiation conduit having an input and output, the input of the initiation conduit isolated from the activation fluid with the activation mechanism in the first position and the input of the initiation conduit communicating with the activation fluid and the output of the initiation conduit communicating with the input of the flow guide with the activation mechanism in the second position such that the activation fluid flows through the initiation conduit to the input of the flow guide.

2. The drug delivery platform of claim 1 further comprising a barrier between the storage structure and the hydrogel, the barrier defining the flow guide.

3. The drug delivery platform of claim 2 wherein the flow guide includes a channel network formed in the barrier.

4. The drug delivery platform of claim 3 wherein the channel network includes a plurality of circular, concentric channels.

5. The drug delivery platform of claim 4 wherein the channel network includes a plurality of generally straight channels extending radially from a common point, the straight channels intersecting at least one of the plurality of concentric, circular channels.

6. The drug delivery platform of claim 4 wherein the flow guide includes a recessed surface formed in the barrier, the recessed surface extending about the plurality of circular, concentric channels.

7. The drug delivery platform of claim 3 wherein the flow guide includes a fluid diverter, the fluid diverter directing fluid from the input of the flow guide to the channel network.

8. A drug delivery platform for delivering a controlled infusion of a drug to an individual, comprising:
    a reservoir for receiving the drug therein;
    an expansion structure positioned adjacent the reservoir, the expansion structure movable between a first configuration and an expanded second configuration wherein the expansion structure exerts a pressure on the reservoir to urge the drug therefrom in response to exposure to a predetermined stimulus;
    a storage structure for housing the predetermined stimulus, the predetermined stimulus in the storage structure being fluidicly isolated from the expansion structure;
    an actuation mechanism movable between a non-actuated position wherein the predetermined stimulus housed in the storage structure is fluidicly isolated from the expansion structure and an actuated position wherein the predetermined stimulus housed in the storage structure communicates with the expansion structure; and
    a flow guide for guiding the predetermined stimulus to the expansion structure in response to the actuation mechanism moving to the actuated position, the flow guide having an input;
    wherein the actuation mechanism includes an initiation conduit having an input and output, the input of the initiation conduit isolated from the activation fluid with the activation mechanism in the non-actuated position and the input of the initiation conduit communicating with the predetermined stimulus and the output of the initiation conduit communicating with an input of the flow guide with the actuation mechanism in the actuated position such that the activation fluid flows through the initiation conduit to the input of the flow guide.

9. The drug delivery platform of claim 8 wherein the expansion structure includes a hydrogel that expands in response to the predetermined stimulus.

10. The drug delivery platform of claim 9 wherein the predetermined stimulus is a fluid.

11. The drug delivery platform of claim 8 wherein the flow guide includes a channel network formed therein.

12. The drug delivery platform of claim 11 wherein the channel network includes a plurality of circular, concentric channels.

13. The drug delivery platform of claim 12 wherein the channel network includes a plurality of generally straight channels extending radially from a common point, the straight channels intersecting at least one of the plurality of concentric, circular channels.

14. The drug delivery platform of claim 12 wherein the flow guide includes a recessed surface formed therein, the recessed surface extending about the plurality of circular, concentric channels.

15. The drug delivery platform of claim 11 wherein the flow guide includes a fluid diverter, the fluid diverter directing fluid from the input of the flow guide to the channel network.

* * * * *